United States Patent
Hu et al.

(10) Patent No.: US 12,194,122 B2
(45) Date of Patent: Jan. 14, 2025

(54) COMBINATION OF MODIFIED STARCH/C13-C15 FATTY ACID/CLAY

(71) Applicant: L'OREAL, Paris (FR)

(72) Inventors: Fan Hu, Kanagawa (JP); Masanori Orita, Kanagawa (JP)

(73) Assignee: L'OREAL, Paris (FR)

( * ) Notice: Subject to any disclaimer, the term of this patent is extended or adjusted under 35 U.S.C. 154(b) by 527 days.

(21) Appl. No.: 17/605,104

(22) PCT Filed: Apr. 7, 2020

(86) PCT No.: PCT/JP2020/016231
§ 371 (c)(1),
(2) Date: Oct. 20, 2021

(87) PCT Pub. No.: WO2020/218044
PCT Pub. Date: Oct. 29, 2020

(65) Prior Publication Data
US 2022/0313571 A1    Oct. 6, 2022

(30) Foreign Application Priority Data
Apr. 24, 2019 (JP) ................. 2019-082850

(51) Int. Cl.
| A61K 8/26 | (2006.01) |
| A61K 8/36 | (2006.01) |
| A61K 8/73 | (2006.01) |
| A61Q 5/00 | (2006.01) |

(52) U.S. Cl.
CPC ............. *A61K 8/26* (2013.01); *A61K 8/361* (2013.01); *A61K 8/732* (2013.01); *A61Q 5/008* (2013.01)

(58) Field of Classification Search
CPC .................................................. A61K 8/732
See application file for complete search history.

(56) References Cited

U.S. PATENT DOCUMENTS

| 2,528,378 | A | 10/1950 | Mannheimer |
| 3,137,592 | A | 6/1964 | Protzman et al. |
| 4,465,702 | A | 8/1984 | Eastman et al. |
| 5,037,929 | A | 8/1991 | Rajagopalan et al. |
| 5,131,953 | A | 7/1992 | Kasica et al. |
| 2006/0182702 | A1 | 8/2006 | Lazzeri et al. |
| 2011/0092405 | A1 * | 4/2011 | Ryklin .......... C11D 1/94  510/159 |

FOREIGN PATENT DOCUMENTS

| CN | 1853610 | A | 11/2006 |
| CN | 1997342 | A | 7/2007 |
| CN | 103327959 | A | 9/2013 |
| EP | 1801194 | A1 * | 6/2007 .............. A61K 8/44 |
| FR | 2976488 | A1 | 12/2012 |
| JP | 2015-209415 | A | 11/2015 |
| WO | 2018/114548 | A1 | 6/2018 |

OTHER PUBLICATIONS

Raphaelides et al. "A process designed for the continuous production of starch inclusion complexes on an industrial scale", Food and Bioproducts Processing, 96 , 2015, 245-244. (Year: 2015).*
Wang, L. et al., "Effects of fatty acid chain length on properties of potato starch-fattyacid complexes under partially gelatinization", Int' J Food Properties, 2018, vol. 21, No. 1, 2121-2134. (Year: 2018).*
PCT, International Search Report for the corresponding patent application No. PCT/JP2020/016231, dated Jul. 13, 2020.
Database GNPD [Online] MINTEL: Oct. 24, 2018, anonymous: "VC Face Wash", XP055710512, Database accession No. 6078311.
Database GNPD [Online] MINTEL: Sep. 4, 2014, anonymous: "Deep Cleansing Foam", XP055710517, Database accession No. 2640771.
Meng et al., Preparation of corn starch-fatty acid complexes by high-pressure homogenization, Starch/Stärke 2014, 66, 809-817.
Cao et al., Preparation of Starch-Fatty Acid Modified Clay and Its Application in Packaging Papers, Ind. Eng. Chem. Res, 2011, 50, 5628-5633.
CNIPA, Office Action dated Apr. 13, 2023 for the corresponding Chinese Patent Application No. 202080030065.4, with English translation, 21 pages.
Intellectual Property in India, "Examination Report" mailed Feb. 1, 2024 for related Indian patent application No. 202117049041 and its English translation, 6 pages.
Office Action for the corresponding Japanese Patent Application No. 2019-082850, mailed May 29, 2023, with machine English translation, 10 pages.
"Mask Duo Be Pure & Be Dewy", ID 5944135, Mintel GNPD[online], Aug. 2018 [Search date May 22, 2023], Internet <https://www.portal.mintel.com>.
"Eye Concentrate", ID 2339343, Mintel GNPD[online], Mar. 2014 [Search date May 22, 2023], Internet <https://www.portal.mintel.com>.

* cited by examiner

*Primary Examiner* — Gina C Justice
(74) *Attorney, Agent, or Firm* — LUCAS & MERCANTI, LLP

(57) ABSTRACT

The present invention relates to a composition, comprising (a) at least one modified starch, (b) at least one $C_{13}$-$C_{15}$ fatty acid, and (c) at least one clay. The amount of each of the ingredients (a) to (c) may be within a specific weight range. The composition according to the present invention is stable, and can be rinsed off from the skin and can leave an enhanced deposition of clay on the skin after rinsing off the composition from the skin.

13 Claims, No Drawings

COMBINATION OF MODIFIED STARCH/C13-C15 FATTY ACID/CLAY

CROSS REFERENCE TO RELATED APPLICATION

This Application is a 371 of PCT/JP2020/016231 filed on Apr. 7, 2020 which, in turn, claimed the priority of Japanese Patent Application No. 2019-082850 filed on Apr. 24, 2019, and both applications are incorporated herein by reference.

TECHNICAL FIELD

The present invention relates to a composition comprising a combination of modified starch, $C_{13}$-$C_{15}$ fatty acid and clay, as well as a use of the composition.

BACKGROUND ART

The use of mineral clays as medicinal and cosmetic tools has been popular for a long time.

Clays are used to absorb excess oil, dirt, and toxins from the skin while simultaneously exfoliating and improving skin circulation. Some clays, such as bentonite clay, are primarily ingested for medicinal purposes such as detoxification or mineral deficiencies.

Other clays, such as French Green clay and Rhassoul clay, are used externally for skin conditions and for cosmetic purposes. Clays come in a variety of colors such as red, green, white, gray, and can range in texture from coarse and heavy to fine and fluffy. The different colors of clays occur because of their natural mineral content.

In modern cosmetics, such clays are used as key active ingredients for oil control products which are sold in the form of oil control face washes, etc. In some rinse off cosmetic compositions, clays are included.

DISCLOSURE OF INVENTION

A rinse off cosmetic composition including clay may leave a deposition of the clay on a keratin substance such as skin even after the composition is rinsed off from the keratin substance. The remaining deposition of clays, if present, can contribute to oil control.

On the other hand, a composition including clay may not be stable such that it may cause a phase separation.

An objective of the present invention is to provide a stable composition which can be rinsed off from a keratin substance such as skin and can leave an enhanced deposition of clay on the keratin substance after rinsing off the composition from the keratin substance.

The above objective can be achieved by a composition, comprising:
(a) at least one modified starch;
(b) at least one $C_{13}$-$C_{15}$ acid; and
(c) at least one clay.

The (a) modified starch may be hydrophobic.

The (a) modified starch may be hydroxyalkyl-modified starch, preferably selected from the group consisting of hydroxyethyl starch, hydroxypropyl starch, hydroxyethyl starch phosphate, hydroxypropyl starch phosphate, and a mixture thereof.

The (b) $C_{13}$-$C_{15}$ fatty acid may be myristic acid

The (c) clay may be kaolin.

The weight ratio of the amount of the (b) $C_{13}$-$C_{15}$ fatty acid/the amount of the (a) modified starch may be 1.1 or more, preferably 1.2 or more, and more preferably 1.3 or more.

The (a) modified starch and the (b) $C_{13}$-$C_{15}$ fatty acid may form a complex.

The (c) clay may be coated with the (a) modified starch and the (b) $C_{13}$-$C_{15}$ fatty acid, preferably a complex formed by the (a) modified starch and the (b) $C_{13}$-$C_{15}$ fatty acid, and more preferably a complex formed by hydrophobic modified starch and myristic acid.

The amount of the (a) modified starch in the composition may be from 0.01% to 15% by weight, preferably from 0.1% to 10% by weight, and more preferably from 0.5% to 5% by weight, relative to the total weight of the composition.

The amount of the (b) $C_{13}$-$C_{15}$ fatty acid may be from 1% to 20% by weight, preferably from 3% to 15% by weight, and more preferably from 5% to 10% by weight, relative to the total weight of the composition.

The amount of the (c) clay may be from 1% to 40% by weight, preferably from 5% to 35% by weight, and more preferably from 10% to 30% by weight, relative to the total weight of the composition.

The composition according to the present invention may further comprise (d) water.

The amount of the (d) water may be from 1% to 50% by weight, preferably from 5% to 40% by weight, and more preferably from 10% to 30% by weight, relative to the total weight of the composition.

The pH of the composition according to the present invention may be more than 7.0, preferably more than 7.5, and more preferably more than 8.0.

The composition according to the present invention may be a cosmetic composition, preferably a rinse-off composition, and more preferably a rinse-off cleansing composition.

The present invention also relates to a cosmetic process for a keratin substance, such as skin, comprising the step of:
applying the composition according to any one of claims 1 to 12 onto the keratin substance.

The present invention also relates to a use of a combination of:
(a) at least one modified starch; and
(b) at least one $C_{13}$-$C_{15}$ fatty acid
in order to increase the deposition on a keratin substance such as skin of (c) at least one clay.

The (a) at least one modified starch and the (b) at least one $C_{13}$-$C_{15}$ fatty acid may form a complex, and preferably the (c) at least one clay is coated with the complex.

BEST MODE FOR CARRYING OUT THE INVENTION

After diligent research, the inventors have discovered that it is possible to provide a stable composition which can be rinsed off from a keratin substance such as skin and can leave an enhanced deposition of clay on the keratin substance after rinsing off the composition from the keratin substance.

The composition according to the present invention comprises a combination of (a) at least one modified starch, (b) at least one $C_{13}$-$C_{15}$ fatty acid, and (c) at least one clay.

The composition according to the present invention is stable such that it does not cause a phase separation for a long period of time.

The composition according to the present invention can be rinsed off from a keratin substance such as skin and can leave an increased amount of a deposition of clay on the keratin substance after rinsing off the composition from the keratin substance.

A deposition of clay can contribute to oil control. Since the composition according to the present invention can increase the amount of the deposition of clay on a keratin substance such as skin, the composition according to the present invention can provide long-lasting oil control effects. Thus, for example, the composition according to the present invention can control or suppress for a long period of time non-preferable events such as greasy appearance caused by oily substances such as sebum on a keratin substance such as skin. Also, the increased amount of the deposition of clay on a keratin substance such as skin can provide a smooth feeling to touch for a long period of time.

The (c) clay may be coated with the (a) modified starch and the (b) $C_{13}$-$C_{15}$ fatty acid. The (a) modified starch and the (b) $C_{13}$-$C_{15}$ fatty acid may form a complex. Thus, the (c) clay may be coated with a complex formed by the (a) modified starch and the (b) $C_{13}$-$C_{15}$ fatty acid. It is preferable that the complex be formed by hydrophobic modified starch and myristic acid.

The hydrophobicity of the (c) clay can be enhanced by the (a) modified starch and the (b) $C_{13}$-$C_{15}$ fatty acid, preferably a complex formed by the (a) modified starch and the (b) $C_{13}$-$C_{15}$ fatty acid, and more preferably a complex formed by hydrophobic modified starch and myristic acid. Therefore, the (c) clay can deposit more on a keratin substance such as skin, due to hydrophobic-hydrophobic interaction between the (c) clay and the keratin substance. This can result in the increase in the amount of the deposition of the (c) clay on the keratin substance.

Hereafter, the present invention will be described in a detailed manner.

[Composition]

One of the aspects of the present invention is a composition, comprising:
(a) at least one modified starch;
(b) at least one $C_{13}$-$C_{15}$ fatty acid; and
(c) at least one clay.

In one embodiment of the present invention,
the amount of the (a) modified starch in the composition is from 0.01% to 15% by weight, preferably from 0.1% to 10% by weight, and more preferably from 0.5% to 5% by weight, relative to the total weight of the composition,
the amount of the (b) $C_{13}$-$C_{15}$ fatty acid is from 1% to 20% by weight, preferably from 3% to 15% by weight, and more preferably from 5% to 10% by weight, relative to the total weight of the composition, and
the amount of the (c) clay is from 1% to 40% by weight, preferably from 5% to 35% by weight, and more preferably from 10% to 30% by weight, relative to the total weight of the composition.

(Modified Starch)

The composition according to the present invention comprises (a) at least one modified starch. A single type of modified starch may be used, or two or more different types of modified starches may be used in combination.

The (a) modified starch may be in the form of a powder. In other words, the (a) modified starch may be in the form of particles. In this case, the particle size of the (a) modified starch is not limited.

It is preferable that the (a) modified starch is film-forming, i.e., is capable of forming a film.

The (a) modified starch is based on a base starch. Base starch, as used herein, is intended to include all starches derived from any native source, any of which may be suitable for use herein. A native starch, as used herein, is one as it is found in nature. Also suitable are starches derived from a plant obtained by standard breeding techniques including crossbreeding, translocation, inversion, transformation or any other method of gene or chromosome engineering to include variations thereof. In addition, starches derived from a plant grown from artificial mutations and variations of the above generic starches, which may be produced by known standard methods of mutation breeding, are also suitable herein.

Typical sources for the starches are cereals, tubers, roots, legumes and fruits. The native source can be waxy varieties of corn (maize), pea, potato, sweet potato, banana, barley, wheat, rice, oat, sago, amaranth, tapioca (cassava), arrowroot, canna, and sorghum, as well as low and high amylose varieties thereof. As used herein, the term "low amylose" starch is intended to include a starch containing no more than about 10%, particularly no more than 5%, and more particularly no more than 2% amylose by weight. As used herein, the term "high amylose" starch is intended to include a starch containing at least about 50%, particularly at least about 70%, and more particularly at least about 80% amylose by weight. High amylose starches may be preferable.

The (a) modified starch may be pre-gelatinized. Pre-gelatinization and techniques for achieving pre-gelatinization are known in the art and disclosed for example in U.S. Pat. Nos. 4,465,702, 5,037,929, 5,131,953, and 5,149,799. Also see, Chapter XXII-"Production and Use of Pregelatinized Starch", Starch: Chemistry and Technology, Vol. III-Industrial Aspects, R. L. Whistler and E. F. Paschall, Editors, Academic Press, New York 1967. The term pre-gelatinized is intended to mean swollen starch particles, which have lost their birefringence and/or maltese crosses in polarized light. Such pre-gelatinized starch derivatives are substantially soluble in cold water without cooking. In this context "soluble" does not necessarily mean the formation of a true molecular solution, but may also mean a colloidal dispersion. In one embodiment, the starch is completely pre-gelatinized.

The pre-gelatinized modified starch is easily and quickly soluble even in cold water.

Pre-gelatinization may be achieved by methods which include, without limitation, drum drying, extrusion and spray drying. In one embodiment, extrusion is used for the simultaneous cooking and drying of the starch (see for example U.S. Pat. No. 3,137,592). This process makes use of the physical processing of a starch/water mixture at elevated temperatures and pressures which brings about the gelatinization of the starch, followed by expansion after leaving the nozzle with sudden evaporation of the water.

In one embodiment, pre-gelatinization is completed to provide good solubility and eliminate undissolved particles, which may give rise to an unpleasant, sandy feel in the composition.

In one embodiment, the starch has a majority of intact starch granules. Aqueous dispersions of pre-gelatinized starch derivatives having a largely intact granular structure typically have a more uniform smooth texture than aqueous dispersions of starches without a granular structure, which may have a slightly gritty feel. In the case of pre-gelatinized starches with an intact granular structure, the native internal structure of the hydrogen bonds is destroyed, but the external shape or form is maintained.

The (a) modified starch may be crosslinked. Crosslinking of the starch chains can be achieved by suitable crosslinking agents, that is, bifunctional compounds. In one embodiment, the crosslinking method used is phosphorylation, in which the starch is reacted with phosphorous oxychloride, phosphorous pentoxide, and/or sodium trimetaphosphate. Two starch chains are crosslinked by an anionic P—O group. The anionic character of the crosslinking sites assists the emulsion-stabilizing action of the starch to be used according to the present invention. In another embodiment, the crosslinking method is by means of $C_4$-$C_{18}$ alkane or alkene dicarboxylic acids which include without limitation $C_4$-$C_8$ alkane dicarboxylic acids, exemplified by adipic acid. The alkane or alkene dicarboxylic acid links two starch chains via ester bonds. It can be in straight or branched chain form. The derivatives may be obtained, for example, by reacting starch with the mixed anhydrides of dicarboxylic acid and acetic acid. In one embodiment, less than 0.1 weight percent based on the dry starch crosslinking agent is used. In another embodiment, about 0.06 to 0.1 weight percent based on the dry starch crosslinking agent is used.

It is preferable that the (a) modified starch be hydrophobic. It is more preferable that the surface of the (a) modified starch be hydrophobic.

The modification to make starch hydrophobic may be performed by grafting hydrophobic functional groups such as $C_{1-6}$ acyl (acetyl), $C_{1-6}$ hydroxyalkyl (hydroxyethyl or hydroxypropyl), carboxymethyl or octenylsuccinic group.

The alkyl moiety of the functional group may have 1 to 6 carbon atoms, preferably 2 to 5 carbon atoms, and more preferably 3 or 4 carbon atoms.

It is preferable that the (a) modified starch be hydroxyalkyl-modified starch.

The position of the hydroxyl group, which is bound to the starch backbone via an alkyl group such as 2 to 6 carbon atoms in the alkyl group, is not critical and can be in the alpha to omega position. In one suitable embodiment, the degree of substitution of the hydroxyalkylation is about 0.08 to 0.3. The degree of substitution is the average number of substituted OH groups of the starch molecule per anhydroglucose unit. The hydroxyalkylation of a starch can be brought about by reacting a native starch with alkylene oxides with the appropriate number of carbon atoms, including without limitation hydroxypropylation by reaction of the starch with propylene oxide. The hydroxyalkyl-modified starch can also contain more than one hydroxyl group per alkyl group.

The hydroxyalkyl-modified starch may be selected from the group consisting of hydroxyethyl starch, hydroxypropyl starch, hydroxyethyl starch phosphate, hydroxypropyl starch phosphate, and a mixture thereof.

The processes for preparing the hydroxyalkyl-modified starch may be conducted in any order. However, one skilled in the art would understand the advantages of certain orders. For example, hydroxypropylation would typically be conducted before crosslinking, if the starch is crosslinked, with phosphorous oxychloride as the typical hydroxypropylation process would destroy some of the crosslinking achieved.

Examples of the hydroxyalkyl-modified starch preferably used in the present invention may include the following:

Hydroxypropyl starch phosphate (pre-gelatinized, corn starch) marketed by Akzo Nobel as Structure ZEA and XL; and Corn starch modified (hydroxypropylated, pre-gelatinized, high amylose) marketed by Akzo Nobel, as AMAZE.

The amount of the (a) modified starch in the composition according to the present invention may be 0.01% by weight or more, preferably 0.1% by weight or more, more preferably 0.5% by weight or more, and even more preferably 1% by weight or more, relative to the total weight of the composition.

On the other hand, the amount of the (a) modified starch in the composition according to the present invention may be 15% by weight or less, preferably 10% by weight or less, more preferably 5% by weight or less, and even more preferably 3% by weight or less, relative to the total weight of the composition.

The amount of the (a) modified starch in the composition according to the present invention may range from 0.01% to 15% by weight, preferably from 0.1% to 10% by weight, more preferably from 0.5% to 5% by weight, and even more preferably from 1% to 3% by weight, relative to the total weight of the composition.

($C_{13}$-$C_{15}$ Fatty Acid)

The composition according to the present invention comprises (b) at least one $C_{13}$-$C_{15}$ fatty acid. A single type of $C_{13}$-$C_{15}$ fatty acid, or two or more different types of $C_{13}$-$C_{15}$ fatty acids may be used in combination.

It is preferable that the (b) $C_{13}$-$C_{15}$ fatty acid is saturated. The saturated $C_{13}$-$C_{15}$ fatty acid can be selected from the group consisting of tridecylic acid (tridecanoic acid), myristic acid (tetradecanoic acid) and pentadecylic acid (pentadecanoic acid).

It is possible that the (b) $C_{13}$-$C_{15}$ fatty acid is unsaturated. The unsaturated $C_{13}$-$C_{15}$ fatty acid can be selected from the group consisting of tridecenoic acid, myristoleic acid (tetradecenoic acid) and pentadecenoic acid.

It is more preferable that the (b) $C_{13}$-$C_{15}$ fatty acid be myristic acid.

The amount of the (b) $C_{13}$-$C_{15}$ fatty acid in the composition according to the present invention may be 1% by weight or more, preferably 3% by weight or more, more preferably 5% by weight or more, and even more preferably 6% by weight or more, relative to the total weight of the composition.

On the other hand, the amount of the (b) $C_{13}$-$C_{15}$ fatty acid in the composition according to the present invention may be 20% by weight or less, preferably 15% by weight or less, more preferably 10% by weight or less, and even more preferably 8% by weight or less, relative to the total weight of the composition.

The amount of the (b) $C_{13}$-$C_{15}$ fatty acid in the composition according to the present invention may range from 1% to 20% by weight, preferably from 3% to 15% by weight, more preferably from 5% to 10% by weight, and even more preferably from 6% to 8% by weight, relative to the total weight of the composition.

The weight ratio of the amount (weight) of the (b) $C_{13}$-$C_{15}$ fatty acid/the amount (weight) of the (a) modified starch may be 1.1 or more, preferably 1.2 or more, and more preferably 1.3 or more.

The (a) modified starch and the (b) $C_{13}$-$C_{15}$ fatty acid may form a complex.

(Clay)

The composition according to the present invention comprises (c) at least one clay. A single type of clay may be used, or two or more different types of clays may be used in combination.

The term "clay" refers to a naturally occurring material composed primarily of fine-grained minerals, which is generally plastic at an appropriate water content and will harden when dried or fired. Although clay usually contains phyllosilicates, it may contain other materials that impart plasticity and harden when dried or fired. Associated phases in clay may include materials that do not impart plasticity and organic matter. A common definition is that in the Penguin Dictionary of Science, namely "finely divided rock materials whose component minerals are various silicates, mainly of magnesium or aluminium". Clay comprises Kaolinite (typically defined as $[Si_4]Al_4O_{10}(OH)_8 \cdot nH_2O$ (n=0 or 4)), Illite (typically defined as $M_x[Si_{6.8}Al_{1.2}]Al_3Fe_{0.025}Mg_{0.75}O_{20}$ $(OH)_4$), Vermiculite (typically defined as $·M_x[Si_7Al]AlFe_{0.05}Mg_{0.5}O_{20}(OH)_4$), Smectite (typically defined as $M_x[Si_8]Al_{3.2}Fe_{0.2}Mg_{0.6}O_{20}(OH)_4$, and Chlorite (typically defined as $(Al(OH)_{2.55})_4[Si_{6.8}AlO_{1.2}]Al_{3.4}Mg_{0.6})_{20}(OH)_4)$.

Another definition, frequently used by chemists is "a naturally occurring sediment or sedimentary rock composed of one or more minerals and accessory compounds, the whole usually being rich in hydrated aluminum silicate, iron or magnesium, hydrated alumina, or iron oxide, predominating in particles of colloidal or near-colloidal size, and commonly developing plasticity when sufficiently pulverized and wetted" (see Kirk-Othmer, Encyclopaedia of Chemical Technology, Volume 5, page 544, 2nd edition, John Wiley and Sons, Inc., New York, N.Y. 1964). Example of clays are given in the book "Clay mineralogy, S. Caillere, S. Henin, M. Rautureau, 2nd edition 1982, Masson". Clays may be of natural or synthetic origin.

Hydrophilic clay includes smectites such as saponites, hectorites, montmorillonites, bentonites, beidellite. Hydrophilic clay includes synthetic hectorites (also called laponites) such as the products sold by the company under the name Laporte Laponite XLG, Laponite RD, Laponite RDS (these products are sodium silicates and magnesium silicates in particular sodium, lithium and magnesium) bentonites such as the product sold under the name Bentone® HC Rheox, magnesium silicates and aluminum products such as hydrated products sold by Vanderbilt Company as ultra Veegum®, Veegum® HS, Veegum® DGT, or calcium silicates, particularly the synthetic form sold by the company under the name Micro-Cel® C.

Fuller's earth consists chiefly of hydrated aluminum silicates that contain metal ions such as magnesium, sodium, and calcium within their structure. Montmorillonite is the principal clay mineral in fuller's earth, but it may contain other minerals such as kaolinite, attapulgite, and palygorskite among other components.

Lipophilic clay means clay swellable in a lipophilic medium, the clay swells and forms a colloidal dispersion. Lipophilic clays include modified clays such as the modified magnesium silicate (Bentone gel VS38 from Rheox) hectorites modified with an ammonium chloride fatty acid $C_{10}$ to $C_{22}$, such as hectorite modified with ammonium chloride disteardimethylammonium (CTFA name: Disteardimonium hectorite) sold under the name "Bentone 38 CE" by Rheox or Bentone® 38V by ELEMENTIS.

The origin of such clay can be natural or synthetic mineral clay such as hectorite, bentonite, and quaternized derivatives thereof, for example which are obtained by reacting the minerals with a quaternary ammonium compound, such as stearalkonium bentonite, hectorites, quaternized hectorites such as Quaternium-18 hectorite, carbonates such as propylene carbonate, bentones, and the like.

The non-limiting of examples of clay which can be used in the present invention are Fuller's earth, Pinatubo volcanic ash mud from Philippines, Aleppo clay from Syria, Pulau tiga volcano mud from Malasiya, Nha Trang mud from Vietnam, White Kaolinite from Korea, Yellow Loess from Korea, Jeju volcanic clay from Korea, Guanziling mud form Taiwan, Wudalianchi volcanic mud from China, Black mud of Yuncheng salt lake from China, mineral mud from Tantou village in China, China clay (Kaolin), Maifan stone from China, Beppu onsen Fango from Japan, Kucha from Japan, Tanakura clay from Japan, Cambrian blue clay from Russia, Blue Lagoon mud from Iceland, Saki lake mud from Ukraine, Karlovy Vary moor mud from Czech Republic, Heviz Georgikon moor mud from Hungry, Alpine moor mud from Austria, Bad Wilsnack mud from Germany, Bavarian mineral slat mountain mud from Germany, Freiburg volcanic ash from Germany, Santorini mud from Greece, Mar Menor mud from Spian, Ischian volcanic mud from Italy, Euganean thermal mud from Italy, Yellow clay-Illite from France, French Green Clay—Montmorrillonite, Calistoga mud from USA, Sacred clay and ormalite from USA, Redmond clay from USA, Arctic mineral mud from Canada, Tulum Mayan clay from Mexico, Glacial clay from Canada, Amazonian white clay from Brazil, El Chillante volcanic thermal mud from Argentina, African healing clay, Australian olive green clay.

It is preferable that the (c) clay be kaolin.

The amount of the (c) clay in the composition according to the present invention may be 1% by weight or more, preferably 5% by weight or more, more preferably 10% by weight or more, and even more preferably 15% by weight or more, relative to the total weight of the composition.

On the other hand, the amount of the (c) clay in the composition according to the present invention may be 40% by weight or less, preferably 35% by weight or less, more preferably 30% by weight or less, and even more preferably 25% by weight or less, relative to the total weight of the composition.

The amount of the (c) clay in the composition according to the present invention may range from 1% to 40% by weight, preferably from 5% to 35% by weight, more preferably from 10% to 30% by weight, and even more preferably from 15% to 25% by weight, relative to the total weight of the composition.

The (c) clay may be coated with the (a) modified starch and the (b) $C_{13}$-$C_{15}$ fatty acid, preferably a complex formed by the (a) modified starch and the (b) $C_{13}$-$C_{15}$ fatty acid, and more preferably a complex formed by hydrophobic modified starch and myristic acid.

(Water)

The composition according to the present invention may further comprise (d) water.

The (d) water can form a carrier of the ingredients (a) to (c) in the composition according to the present invention.

The amount of the (d) water may be 1% by weight or more, preferably 5% by weight or more, and more preferably 10% by weight or more, relative to the total weight of the composition.

The amount of the (d) water may be 50% by weight or less, preferably 40% by weight or less, and more preferably 30% by weight or less, relative to the total weight of the composition.

The amount of the (d) water may be from 1% to 50% by weight, preferably from 5% to 40% by weight, and more preferably from 10% to 30% by weight, relative to the total weight of the composition.

(pH)

The pH of the composition according to the present invention may be adjusted to the desired value using acidifying or basifying agents commonly used in dyeing keratin fibers or else using conventional buffer systems.

The composition according to the present invention may be acidic. For example, the pH of the composition according to the present invention may be less than 7.0, more preferably less than 6.5, and even more preferably less than 6.0.

Alternatively, the composition according to the present invention may be basic. For example, the pH of the composition according to the present invention may be more than 7.0, more preferably more than 7.5, and even more preferably more than 8.0.

Among the acidifying agents, mention may be made, by way of example, of mineral or organic acids such as hydrochloric acid, ortho-phosphoric acid, sulfuric acid, carboxylic acids such as acetic acid, tartaric acid, citric acid, and lactic acid, and sulfonic acids.

Among the basifying agents, mention may be made, by way of example, of ammonium hydroxide, alkali metal carbonates, alkanolamines such as mono-, di- and triethanolamines and also their derivatives, alkali metal hydroxides such as sodium or potassium hydroxide and compounds of the formula below:

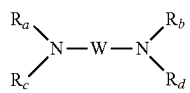

wherein

W denotes an alkylene such as propylene optionally substituted by a hydroxyl or a $C_1$-$C_4$ alkyl radical, and $R_a$, $R_b$, $R_c$ and $R_d$ independently denote a hydrogen atom, an alkyl radical or a $C_1$-$C_4$ hydroxyalkyl radical, which may be exemplified by 1,3-propanediamine and derivatives thereof.

The acidifying or basifying agent may be used in an amount of 20% by weight or less, preferably 15% by weight or less, and more preferably 10% by weight or less, relative to the total weight of the composition.

The acidifying or basifying agent may be used in an amount of 0.001% by weight or more, preferably 0.01% by weight or more, and more preferably 0.1% by weight or more, relative to the total weight of the composition.

The acidifying or basifying agent may be used in an amount ranging from 0.001% to 20% by weight, preferably from 0.01% to 15% by weight, and more preferably from 0.1% to 10% by weight, relative to the total weight of the composition.

(Surfactant)

The composition according to the present invention may further comprise at least one surfactant. Two or more surfactants may be used. Thus, a single type of surfactant or a combination of different types of surfactants may be used.

Any surfactant may be used for the present invention. The surfactant may be selected from the group consisting of anionic surfactants, amphoteric surfactants, cationic surfactants and nonionic surfactants. Two or more surfactants may be used in combination. Thus, a single type of surfactant or a combination of different types of surfactants may be used.

According to one embodiment of the present invention, the amount of the surfactant(s) may range from 0.01% to 35% by weight, preferably from 0.1% to 30% by weight, and more preferably from 1% to 25% by weight, relative to the total weight of the composition according to the present invention.

(i) Anionic Surfactants

The composition may comprise at least one anionic surfactant. Two or more anionic surfactants may be used in combination.

It is preferable that the anionic surfactant be selected from the group consisting of ($C_6$-$C_{30}$)alkyl sulfates, ($C_6$-$C_{30}$)alkyl ether sulfates, ($C_6$-$C_{30}$)alkylamido ether sulfates, alkylaryl polyether sulfates, monoglyceride sulfates; ($C_6$-$C_{30}$)alkylsulfonates, ($C_6$-$C_{30}$)alkylamide sulfonates, ($C_6$-$C_{30}$)alkylaryl sulfonates, α-olefin sulfonates, paraffin sulfonates; ($C_6$-$C_{30}$)alkyl phosphates; ($C_6$-$C_{30}$)alkyl sulfosuccinates, ($C_6$-$C_{30}$)alkyl ether sulfosuccinates, ($C_6$-$C_{30}$)alkylamide sulfosuccinates; ($C_6$-$C_{30}$)alkyl sulfoacetates; ($C_6$-$C_{24}$)acyl sarcosinates; ($C_6$-$C_{24}$)acyl glutamates; ($C_6$-$C_{30}$)alkylpolyglycoside carboxylic ethers; ($C_6$-$C_{30}$)alkylpolyglycoside sulfosuccinates; ($C_6$-$C_{30}$)alkyl sulfosuccinamates; ($C_6$-$C_{24}$) acyl isethionates; N—($C_6$-$C_{24}$)acyl taurates; $C_6$-$C_{30}$ fatty acid (other than the (b) $C_{13}$-$C_{15}$ fatty acid) salts; coconut oil acid salts or hydrogenated coconut oil acid salts; ($C_8$-$C_{20}$) acyl lactylates; ($C_6$-$C_{30}$)alkyl-D-galactoside uronic acid salts; polyoxyalkylenated ($C_6$-$C_{30}$)alkyl ether carboxylic acid salts; polyoxyalkylenated ($C_6$-$C_{30}$)alkylaryl ether carboxylic acid salts; and polyoxyalkylenated ($C_6$-$C_{30}$)alkylamido ether carboxylic acid salts; and corresponding acid forms.

In at least one embodiment, the anionic surfactants are in the form of salts such as salts of alkali metals, for instance sodium; salts of alkaline-earth metals, for instance magnesium; ammonium salts; amine salts; and amino alcohol salts. Depending on the conditions, they may also be in acid form.

It is more preferable that the anionic surfactant be selected from salts of $C_6$-$C_{30}$ fatty acids other than the (b) $C_{13}$-$C_{15}$ fatty acids, ($C_6$-$C_{30}$)alkyl sulfates, ($C_6$-$C_{30}$)alkyl ether sulfates or polyoxyalkylenated ($C_6$-$C_{30}$)alkyl ether carboxylic acids, salified or not.

(ii) Amphoteric Surfactants

The composition may comprise at least one amphoteric surfactant. Two or more amphoteric surfactants may be used in combination.

The amphoteric or zwitterionic surfactants can be, for example (non-limiting list), amine derivatives such as aliphatic secondary or tertiary amine, and optionally quaternized amine derivatives, in which the aliphatic radical is a linear or branched chain including 8 to 22 carbon atoms and containing at least one water-solubilizing anionic group (for example, carboxylate, sulphonate, sulphate, phosphate or phosphonate).

The amphoteric surfactant may preferably be selected from the group consisting of betaines and amidoaminecarboxylated derivatives.

It is preferable that the amphoteric surfactant be selected from betaine-type surfactants.

The betaine-type amphoteric surfactant is preferably selected from the group consisting of alkylbetaines, alkylamidoalkylbetaines, sulfobetaines, phosphobetaines, and alkylamidoalkylsulfobetaines, in particular, ($C_8$-$C_{24}$)alkylbetaines, ($C_8$-$C_{24}$)alkylamido($C_1$-$C_8$)alkylbetaines, sulphobetaines, and ($C_8$-$C_{24}$)alkylamido($C_1$-$C_8$)alkylsulphobetaines. In one embodiment, the amphoteric surfactants of betaine type are chosen from ($C_8$-$C_{24}$)alkylbetaines, ($C_8$-$C_{24}$)alkylamido($C_1$-$C_8$)alkylsulphobetaines, sulphobetaines, and phosphobetaines.

Non-limiting examples that may be mentioned include the compounds classified in the CTFA International Cosmetic Ingredient Dictionary & Handbook, 15th Edition, 2014, under the names cocobetaine, laurylbetaine, cetylbetaine, coco/oleamidopropylbetaine, cocamidopropylbetaine, palmitamidopropylbetaine, stearamidopropylbetaine, cocamidoethylbetaine, cocamidopropylhydroxysultaine, oleamidopropylhydroxysultaine, cocohydroxysultaine, laurylhydroxysultaine, and cocosultaine, alone or as mixtures.

The betaine-type amphoteric surfactant is preferably an alkylbetaine and an alkylamidoalkylbetaine, in particular cocobetaine and cocamidopropylbetaine.

Among the amidoaminecarboxylated derivatives, mention may be made of the products sold under the name Miranol, as described in U.S. Pat. Nos. 2,528,378 and 2,781,354 and classified in the CTFA dictionary, 3rd edition, 1982 (the disclosures of which are incorporated herein by reference), under the names Amphocarboxyglycinates and Amphocarboxypropionates, with the respective structures:

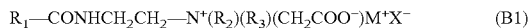

in which:
$R_1$ denotes an alkyl radical of an acid $R_1$—COOH present in hydrolysed coconut oil, a heptyl, nonyl or undecyl radical,
$R_2$ denotes a beta-hydroxyethyl group,
$R_3$ denotes a carboxymethyl group,
$M^+$ denotes a cationic ion derived from alkaline metals such as sodium; ammonium ion; or an ion derived from an organic amine;
$X^-$ denotes an organic or inorganic anionic ion such as halides, acetates, phosphates, nitrates, alkyl($C_1$-$C_4$)sulfates, alkyl($C_1$-$C_4$)- or alkyl($C_1$-$C_4$)aryl-sulfonates, particularly methyl sulfate and ethylsulfate; or $M^+$ and $X^-$ are not present;

in which:
$R_1'$ denotes an alkyl radical of an acid $R_1'$—COOH present in coconut oil or in hydrolysed linseed oil, an alkyl radical, such as a $C_7$, $C_9$, $C_{11}$ or $C_{13}$ alkyl radical, a $C_{17}$ alkyl radical and its iso-form, or an unsaturated $C_{17}$ radical,
B represents —$CH_2CH_2OX'$,
C represents —$(CH_2)_z$—Y', with z=1 or 2,
X' denotes a —$CH_2$—COOH group, —$CH_2$—COOZ', —$CH_2CH_2$—COOH, —$CH_2CH_2$—COOZ' or a hydrogen atom, and
Y' denotes —COOH, —COOZ', —$CH_2$—CHOH—$SO_3Z'$, —$CH_2$—CHOH—$SO_3H$ radical or a —$CH_2$—CH(OH)—$SO_3$—Z' radical,
wherein Z' represents an ion of an alkaline or alkaline earth metal such as sodium, an ion derived from an organic amine or an ammonium ion;
and

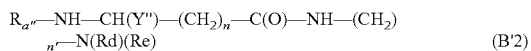

in which:
Y" denotes —C(O)OH, —C(O)OZ", —$CH_2$—CH(OH)—$SO_3H$ or —$CH_2$—CH(OH)—$SO_3$—Z", wherein
Z" denotes a cationic ion derived from alkaline metal or alkaline-earth metals such as sodium, an ion derived from organic amine or an ammonium ion;
Rd and Re denote a $C_1$-$C_4$ alkyl or $C_1$-$C_4$ hydroxyalkyl radical;
$R_{a''}$ denotes a $C_{10}$-$C_{30}$ group alkyl or alkenyl group from an acid, and
n and n' independently denote an integer from 1 to 3.
It is preferable that the amphoteric surfactant with formula B1 and B2 be selected from ($C_8$-$C_{24}$)-alkyl amphomonoacetates, ($C_8$-$C_{24}$)alkyl amphodiacetates, ($C_8$-$C_{24}$)alkyl amphomonopropionates, and ($C_8$-$C_{24}$)alkyl amphodipropionates These compounds are classified in the CTFA dictionary, 5th edition, 1993, under the names Disodium Cocoamphodiacetate, Disodium Lauroamphodiacetate, Disodium Caprylamphodiacetate, Disodium Capryloamphodiacetate, Disodium Cocoamphodipropionate, Disodium Lauroamphopropionate, Disodium Caprylamphodipropionate, Disodium Caprylamphodipropionate, Lauroamphodipropionic acid and Cocoamphodipropionic acid.

By way of example, mention may be made of the cocoamphodiacetate sold under the trade name Miranol® $C_2M$ concentrate by the company Rhodia Chimie.

Among compounds of formula (B'2), mention may be made of sodium diethylaminopropyl cocoaspartamide (CTFA) marketed by CHIMEX under the denomination CHIMEXANE HB.

(iii) Cationic Surfactants

The composition may comprise at least one cationic surfactant. Two or more cationic surfactants may be used in combination.

The cationic surfactant may be selected from the group consisting of optionally polyoxyalkylenated, primary, secondary or tertiary fatty amine salts, quaternary ammonium salts, and mixtures thereof.

Examples of quaternary ammonium salts that may be mentioned include, but are not limited to:
those of general formula (B3) below:

wherein
$R_1$, $R_2$, $R_3$, and $R_4$, which may be identical or different, are chosen from linear and branched aliphatic radicals including from 1 to 30 carbon atoms and optionally including heteroatoms such as oxygen, nitrogen, sulfur and halogens. The aliphatic radicals may be chosen, for example, from alkyl, alkoxy, $C_2$-$C_6$ polyoxyalkylene, alkylamide, ($C_{12}$-$C_{22}$)alkylamido($C_2$-$C_6$)alkyl, ($C_{12}$-$C_{22}$)alkylacetate and hydroxyalkyl radicals; and aromatic radicals such as aryl and alkylaryl; and $X^-$ is chosen from halides, phosphates, acetates, lactates, ($C_2$-$C_6$) alkyl sulfates and alkyl- or alkylaryl-sulfonates;
quaternary ammonium salts of imidazoline, for instance those of formula (B4) below:

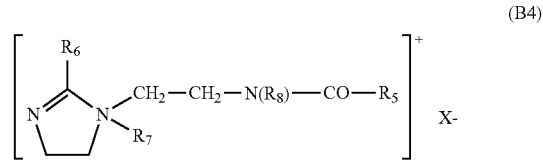

wherein:
$R_5$ is chosen from alkenyl and alkyl radicals including from 8 to 30 carbon atoms, for example fatty acid derivatives of tallow or of coconut;
$R_6$ is chosen from hydrogen, $C_1$-$C_4$ alkyl radicals, and alkenyl and alkyl radicals including from 8 to 30 carbon atoms;
$R_7$ is chosen from $C_1$-$C_4$ alkyl radicals;
$R_8$ is chosen from hydrogen and $C_1$-$C_4$ alkyl radicals; and
$X^-$ is chosen from halides, phosphates, acetates, lactates, alkyl sulfates, alkyl sulfonates, and alkylaryl sulfonates. In one embodiment, $R_5$ and $R_6$ are, for example, a mixture of radicals chosen from alkenyl and alkyl radicals including from 12 to 21 carbon atoms, such as fatty acid derivatives of tallow, $R_7$ is methyl and $R_8$ is hydrogen. Examples of such products include, but are not limited to, Quaternium-27 (CTFA 1997) and Quaternium-83 (CTFA 1997), which are sold under the names "Rewoquat®" W75, W90, W75PG and W75HPG by the company Witco;

di or tri quaternary ammonium salts of formula (B5):

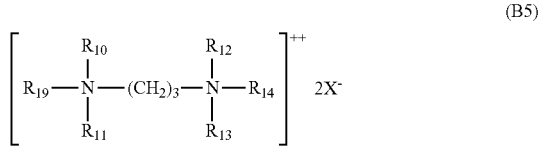
(B5)

wherein:

$R_9$ is chosen from aliphatic radicals including from 16 to 30 carbon atoms;

$R_{10}$ is chosen from hydrogen or alkyl radicals including from 1 to 4 carbon atoms or the group $-(CH_2)_3(R_{16a})(R_{17a})(R_{18a})N^+X^-$;

$R_{11}$, $R_{12}$, $R_{13}$, $R_{14}$, $R_{16a}$, $R_{17a}$, and $R_{18a}$, which may be identical or different, are chosen from hydrogen and alkyl radicals including from 1 to 4 carbon atoms; and $X^-$ is chosen from halides, acetates, phosphates, nitrates, ethyl sulfates, and methyl sulfates.

An example of one such diquaternary ammonium salt is FINQUAT CT-P of FINETEX (Quaternium-89) or FINQUAT CT (Quaternium-75); and quaternary ammonium salts including at least one ester function, such as those of formula (B6) below:

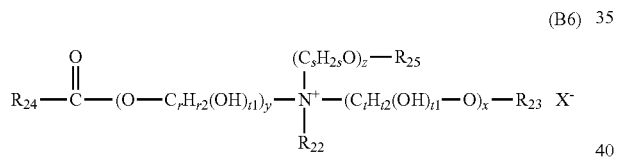
(B6)

wherein:

$R_{22}$ is chosen from $C_1$-$C_6$ alkyl radicals and $C_1$-$C_6$ hydroxyalkyl and dihydroxyalkyl radicals;

$R_{23}$ is chosen from:
the radical below:

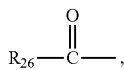, linear and branched, saturated and unsaturated $C_1$-$C_{22}$ hydrocarbon-based radicals $R_{27}$, and hydrogen, $R_{25}$ is chosen from:
the radical below:

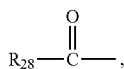, linear and branched, saturated and unsaturated $C_1$-$C_6$ hydrocarbon-based radicals $R_{29}$, and hydrogen, $R_{24}$, $R_{26}$, and $R_{28}$, which may be identical or different, are chosen from linear and branched, saturated and unsaturated, $C_7$-$C_{21}$, hydrocarbon-based radicals;

r, s, and t, which may be identical or different, are chosen from integers ranging from 2 to 6;

each of r1 and t1, which may be identical or different, is 0 or 1, and r2+r1=2r and t1+t2=2t;

y is chosen from integers ranging from 1 to 10;

x and z, which may be identical or different, are chosen from integers ranging from 0 to 10;

$X^-$ is chosen from simple and complex, organic and inorganic anions; with the proviso that the sum x+y+z ranges from 1 to 15, that when x is 0, R23 denotes R27, and that when z is 0, R25 denotes R29. R22 may be chosen from linear and branched alkyl radicals. In one embodiment, $R_{22}$ is chosen from linear alkyl radicals. In another embodiment, R22 is chosen from methyl, ethyl, hydroxyethyl, and dihydroxypropyl radicals, for example methyl and ethyl radicals. In one embodiment, the sum x+y+z ranges from 1 to 10. When Rn is a hydrocarbon-based radical $R_{27}$, it may be long and include from 12 to 22 carbon atoms, or short and include from 1 to 3 carbon atoms. When $R_{25}$ is a hydrocarbon-based radical $R_{29}$, it may include, for example, from 1 to 3 carbon atoms. By way of a non-limiting example, in one embodiment, R24, R26, and R28, which may be identical or different, are chosen from linear and branched, saturated and unsaturated, $C_{11}$-$C_{21}$ hydrocarbon-based radicals, for example from linear and branched, saturated and unsaturated $C_{11}$-$C_{21}$ alkyl and alkenyl radicals. In another embodiment, x and z, which may be identical or different, are 0 or 1. In one embodiment, y is equal to 1. In another embodiment, r, s and t, which may be identical or different, are equal to 2 or 3, for example equal to 2. The anion $X^-$ may be chosen from, for example, halides, such as chloride, bromide, and iodide; and $C_1$-$C_4$ alkyl sulfates, such as methyl sulfate. However, methanesulfonate, phosphate, nitrate, tosylate, an anion derived from an organic acid, such as acetate and lactate, and any other anion that is compatible with the ammonium including an ester function, are other non-limiting examples of anions that may be used according to the present invention. In one embodiment, the anion $X^-$ is chosen from chloride and methyl sulfate.

In another embodiment, the ammonium salts of formula (B6) may be used, wherein:

$R_{22}$ is chosen from methyl and ethyl radicals, x and y are equal to 1;

z is equal to 0 or 1;

r, s and t are equal to 2;

R23 is chosen from:
the radical below:

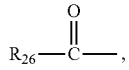, methyl, ethyl, and $C_{14}$-$C_{22}$ hydrocarbon-based radicals, hydrogen;

$R_{25}$ is chosen from:
the radical below:

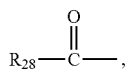, and hydrogen;

$R_{24}$, $R_{26}$, and $R_{28}$, which may be identical or different, are chosen from linear and branched, saturated and unsaturated, $C_{13}$-$C_{17}$ hydrocarbon-based radicals, for example from linear and branched, saturated and unsaturated, $C_{13}$-$C_{17}$ alkyl and alkenyl radicals.

In one embodiment, the hydrocarbon-based radicals are linear.

Non-limiting examples of compounds of formula (B6) that may be mentioned include salts, for example chloride and methyl sulfate, of diacyloxyethyl-dimethylammonium, of diacyloxyethyl-hydroxyethyl-methylammonium, of mono acyloxyethyl-dihydroxyethyl-methylammonium, of triacyloxyethyl-methylammonium, of monoacyloxyethyl-hydroxyethyl-dimethyl-ammonium, and mixtures thereof. In one embodiment, the acyl radicals may include from 14 to 18 carbon atoms, and may be derived, for example, from a plant oil, for instance palm oil and sunflower oil. When the compound includes several acyl radicals, these radicals may be identical or different.

These products may be obtained, for example, by direct esterification of optionally oxyalkylenated triethanolamine, triisopropanolamine, alkyldiethanolamine or alkyldiisopropanolamine onto fatty acids or onto mixtures of fatty acids of plant or animal origin, or by transesterification of the methyl esters thereof. This esterification may be followed by a quaternization using an alkylating agent chosen from alkyl halides, for example methyl and ethyl halides; dialkyl sulfates, for example dimethyl and diethyl sulfates; methyl methanesulfonate; methyl para-toluenesulfonate; glycol chlorohydrin; and glycerol chlorohydrin.

Such compounds are sold, for example, under the names Dehyquart® by the company Cognis, Stepanquat® by the company Stepan, Noxamium® by the company Ceca, and "Rewoquat® WE 18" by the company Rewo-Goldschmidt.

Other non-limiting examples of ammonium salts that may be used in the composition according to the present invention include the ammonium salts including at least one ester function described in U.S. Pat. Nos. 4,874,554 and 4,137,180.

The quaternary ammonium salts mentioned above that may be used in the composition according to the present invention include, but are not limited to, those corresponding to formula (I), for example tetraalkylammonium chlorides, for instance dialkyldimethylammonium and alkyltrimethylammonium chlorides in which the alkyl radical includes from about 12 to 22 carbon atoms, such as behenyltrimethylammonium, distearyldimethylammonium, cetyltrimethylammonium and benzyldimethylstearylammonium chloride; palmitylamidopropyltrimethylammonium chloride; and stearamidopropyldimethyl(myristyl acetate) ammonium chloride, sold under the name "Ceraphyl® 70" by the company Van Dyk.

According to one embodiment, the cationic surfactant that may be used in the composition according to the present invention is chosen from behenyltrimethylammonium chloride, cetyltrimethylammonium chloride, Quaternium-83, Quaternium-87, Quaternium-22, behenylamidopropyl-2,3-dihydroxypropyldimethylammonium chloride, palmitylamidopropyltrimethylammonium chloride, and stearamidopropyldimethylamine.

(iv) Nonionic Surfactants

The composition comprises at least one nonionic surfactant. Two or more nonionic surfactants may be used in combination.

The nonionic surfactants are compounds well known in themselves (see, e.g., in this regard, "Handbook of Surfactants" by M. R. Porter, Blackie & Son publishers (Glasgow and London), 1991, pp. 116-178). Thus, they can, for example, be chosen from alcohols, alpha-diols, alkylphenols and esters of fatty acids, these compounds being ethoxylated, propoxylated or glycerolated and having at least one fatty chain comprising, for example, from 8 to 30 carbon atoms, it being possible for the number of ethylene oxide or propylene oxide groups to range from 2 to 50, and for the number of glycerol groups to range from 1 to 30. Maltose derivatives may also be mentioned. Non-limiting mention may also be made of copolymers of ethylene oxide and/or of propylene oxide; condensates of ethylene oxide and/or of propylene oxide with fatty alcohols; polyethoxylated fatty amides comprising, for example, from 2 to 30 mol of ethylene oxide; polyglycerolated fatty amides comprising, for example, from 1.5 to 5 glycerol groups, such as from 1.5 to 4; ethoxylated fatty acid esters of sorbitan comprising from 2 to 30 mol of ethylene oxide; ethoxylated oils of plant origin; fatty acid esters of sucrose; fatty acid esters of polyethylene glycol; polyethoxylated fatty acid mono or diesters of glycerol ($C_6$-$C_{24}$)alkylpolyglycosides; N—($C_6$-$C_{24}$)alkylglucamine derivatives; amine oxides such as ($C_{10}$-$C_{14}$)alkylamine oxides or N—($C_{10}$-$C_{14}$)acylaminopropylmorpholine oxides; silicone surfactants; and mixtures thereof.

The nonionic surfactants may preferably be chosen from monooxyalkylenated, polyoxyalkylenated, monoglycerolated or polyglycerolated nonionic surfactants. The oxyalkylene units are more particularly oxyethylene or oxypropylene units, or a combination thereof, and are preferably oxyethylene units.

Examples of monooxyalkylenated or polyoxyalkylenated nonionic surfactants that may be mentioned include:

monooxyalkylenated or polyoxyalkylenated ($C_8$-$C_{24}$)alkylphenols, saturated or unsaturated, linear or branched, monooxyalkylenated or polyoxyalkylenated $C_8$-$C_{30}$ alcohols, saturated or unsaturated, linear or branched, monooxyalkylenated or polyoxyalkylenated $C_8$-$C_{30}$ amides, esters of saturated or unsaturated, linear or branched, $C_8$-$C_{30}$ acids and of polyalkylene glycols, monooxyalkylenated or polyoxyalkylenated esters of saturated or unsaturated, linear or branched, $C_8$-$C_{30}$ acids and of sorbitol, saturated or unsaturated, monooxyalkylenated or polyoxyalkylenated plant oils, condensates of ethylene oxide and/or of propylene oxide, inter alia, alone or as mixtures.

The surfactants preferably contain a number of moles of ethylene oxide and/or of propylene oxide of between 1 and 100 and most preferably between 2 and 50. According to one of the embodiments of the present invention, the polyoxyalkylenated nonionic surfactants are chosen from polyoxyethylenated fatty alcohol (polyethylene glycol ether of fatty alcohol) and polyoxyethylenated fatty ester (polyethylene glycol ester of fatty acid).

Examples of polyoxyethylenated saturated fatty alcohol (or $C_8$-$C_{30}$ alcohols) that may be mentioned include the adducts of ethylene oxide with lauryl alcohol, especially those containing from 9 to 50 oxyethylene units and more particularly those containing from 10 to 12 oxyethylene units (Laureth-10 to Laureth-12, as the CTFA names); the adducts of ethylene oxide with behenyl alcohol, especially those containing from 9 to 50 oxyethylene units (Beheneth-9 to Beheneth-50, as the CTFA names); the adducts of ethylene oxide with cetearyl alcohol (mixture of cetyl alcohol and stearyl alcohol), especially those containing from 10 to 30 oxyethylene units (Ceteareth-10 to Ceteareth-30, as the CTFA names); the adducts of ethylene oxide with cetyl alcohol, especially those containing from 10 to 30 oxyethylene units (Ceteth-10 to Ceteth-30, as the CTFA names); the adducts of ethylene oxide with stearyl alcohol, especially those containing from 10 to 30 oxyethylene units (Steareth-10 to Steareth-30, as the CTFA names); the adducts of ethylene oxide with isostearyl alcohol, especially those containing from 10 to 50 oxyethylene units (Isosteareth-10 to Isosteareth-50, as the CTFA names); and mixtures thereof.

Examples of polyoxyethylenated unsaturated fatty alcohol (or $C_8$-$C_{30}$ alcohols) that may be mentioned include the adducts of ethylene oxide with oleyl alcohol, especially those containing from 2 to 50 oxyethylene units and more particularly those containing from 10 to 40 oxyethylene units (Oleth-10 to Oleth-40, as the CTFA names); and mixtures thereof.

As examples of monoglycerolated or polyglycerolated nonionic surfactants, monoglycerolated or polyglycerolated $C_8$-$C_{40}$ alcohols are preferably used.

In particular, the monoglycerolated or polyglycerolated $C_8$-$C_{40}$ alcohols correspond to the following formula:

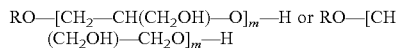

$$RO\text{---}[CH_2\text{---}CH(CH_2OH)\text{---}O]_m\text{---}H \text{ or } RO\text{---}[CH(CH_2OH)\text{---}CH_2O]_m\text{---}H$$

in which R represents a linear or branched $C_8$-$C_{40}$ and preferably $C_8$-$C_{30}$ alkyl or alkenyl radical, and m represents a number ranging from 1 to 30 and preferably from 1.5 to 10.

As examples of compounds that are suitable in the context of the present invention, mention may be made of lauryl alcohol containing 4 mol of glycerol (INCI name: Polyglyceryl-4 Lauryl Ether), lauryl alcohol containing 1.5 mol of glycerol, oleyl alcohol containing 4 mol of glycerol (INCI name: Polyglyceryl-4 Oleyl Ether), oleyl alcohol containing 2 mol of glycerol (INCI name: Polyglyceryl-2 Oleyl Ether), cetearyl alcohol containing 2 mol of glycerol, cetearyl alcohol containing 6 mol of glycerol, oleocetyl alcohol containing 6 mol of glycerol, and octadecanol containing 6 mol of glycerol.

The alcohol may represent a mixture of alcohols in the same way that the value of m represents a statistical value, which means that, in a commercial product, several species of polyglycerolated fatty alcohol may coexist in the form of a mixture.

Among the monoglycerolated or polyglycerolated alcohols, it is preferable to use the $C_8/C_{10}$ alcohol containing 1 mol of glycerol, the $C_{10}/C_{12}$ alcohol containing 1 mol of glycerol and the $C_{12}$ alcohol containing 1.5 mol of glycerol.

The monoglycerolated or polyglycerolated $C_8$-$C_{40}$ fatty esters may correspond to the following formula:

$$R'O\text{---}[CH_2\text{---}CH(CH_2OR''')\text{---}O]_m\text{---}R'' \text{ or } R'O\text{---}[CH(CH_2OR''')\text{---}CH_2O]_m\text{---}R''$$

in which each of R', R" and R''' independently represents a hydrogen atom, or a linear or branched $C_8$-$C_{40}$ and preferably $C_8$-$C_{30}$ alkyl-CO- or alkenyl-CO-radical, with the proviso that at least one of R', R" and R''' is not a hydrogen atom, and m represents a number ranging from 1 to 30 and preferably from 1.5 to 10.

Examples of polyoxyethylenated fatty esters that may be mentioned include the adducts of ethylene oxide with esters of lauric acid, palmitic acid, stearic acid or behenic acid, and mixtures thereof, especially those containing from 9 to 100 oxyethylene units, such as PEG-9 to PEG-50 laurate (CTFA names: PEG-9 laurate to PEG-50 laurate); PEG-9 to PEG-50 palmitate (CTFA names: PEG-9 palmitate to PEG-50 palmitate); PEG-9 to PEG-50 stearate (CTFA names: PEG-9 stearate to PEG-50 stearate); PEG-9 to PEG-50 palmitostearate; PEG-9 to PEG-50 behenate (CTFA names: PEG-9 behenate to PEG-50 behenate); polyethylene glycol 100 EO monostearate (CTFA name: PEG-100 stearate); and mixtures thereof.

According to one of the embodiments of the present invention, the nonionic surfactant may be selected from esters of polyols with fatty acids with a saturated or unsaturated chain containing for example from 8 to 24 carbon atoms, preferably 12 to 22 carbon atoms, and polyoxyalkylenated derivatives thereof, preferably containing from 10 to 200, and more preferably from 10 to 100 oxyalkylene units, such as glyceryl esters of a $C_8$-$C_{24}$, preferably $C_{12}$-$C_{22}$, fatty acid or acids and polyoxyalkylenated derivatives thereof, preferably containing from 10 to 200, and more preferably from 10 to 100 oxyalkylene units; sorbitol esters of a $C_8$-$C_{24}$, preferably $C_{12}$-$C_{22}$, fatty acid or acids and polyoxyalkylenated derivatives thereof, preferably containing from 10 to 200, and more preferably from 10 to 100 oxyalkylene units; sugar (sucrose, maltose, glucose, fructose, and/or alkylglycose) esters of a $C_8$-$C_{24}$, preferably $C_{12}$-$C_{22}$, fatty acid or acids and polyoxyalkylenated derivatives thereof, preferably containing from 10 to 200, and more preferably from 10 to 100 oxyalkylene units; ethers of fatty alcohols; ethers of sugar and a $C_8$-$C_{24}$, preferably $C_{12}$-$C_{22}$, fatty alcohol or alcohols; and mixtures thereof.

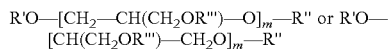

As glyceryl esters of fatty acids, glyceryl stearate (glyceryl mono-, di- and/or tristearate) (CTFA name: glyceryl stearate), glyceryl laurate or glyceryl ricinoleate and mixtures thereof can be cited, and as polyoxyalkylenated derivatives thereof, mono-, di- or triester of fatty acids with a polyoxyalkylenated glycerol (mono-, di- or triester of fatty acids with a polyalkylene glycol ether of glycerol), preferably polyoxyethylenated glyceryl stearate (mono-, di- and/or tristearate), such as PEG-20 glyceryl stearate (mono-, di- and/or tristearate) can be cited.

Mixtures of these surfactants, such as for example the product containing glyceryl stearate and PEG-100 stearate, marketed under the name ARLACEL 165 by Uniqema, and the product containing glyceryl stearate (glyceryl mono- and distearate) and potassium stearate marketed under the name TEGIN by Goldschmidt (CTFA name: glyceryl stearate SE), can also be used.

The sorbitol esters of $C_8$-$C_{24}$ fatty acids and polyoxyalkylenated derivatives thereof can be selected from sorbitan palmitate, sorbitan isostearate, sorbitan trioleate and esters of fatty acids and alkoxylated sorbitan containing for example from 20 to 100 EO, such as for example sorbitan monostearate (CTFA name: sorbitan stearate), sold by the company ICI under the name Span 60, sorbitan monopalmitate (CTFA name: sorbitan palmitate), sold by the company ICI under the name Span 40, and sorbitan tristearate 20 EO (CTFA name: polysorbate 65), sold by the company ICI under the name Tween 65, polyethylene sorbitan trioleate (polysorbate 85) or the compounds marketed under the trade names Tween 20 or Tween 60 by Uniqema.

As esters of fatty acids and glucose or alkylglucose, glucose palmitate, alkylglucose sesquistearates such as methylglucose sesquistearate, alkylglucose palmitates such as methylglucose or ethylglucose palmitate, methylglucoside fatty esters, the diester of methylglucoside and oleic acid (CTFA name: Methyl glucose dioleate), the mixed ester of methylglucoside and the mixture of oleic acid/hydroxystearic acid (CTFA name: Methyl glucose dioleate/hydroxystearate), the ester of methylglucoside and isostearic acid (CTFA name: Methyl glucose isostearate), the ester of methylglucoside and lauric acid (CTFA name: Methyl glucose laurate), the mixture of monoester and diester of methylglucoside and isostearic acid (CTFA name: Methyl glucose sesqui-isostearate), the mixture of monoester and diester of methylglucoside and stearic acid (CTFA name: Methyl glucose sesquistearate) and in particular the product marketed under the name Glucate SS by AMERCHOL, and mixtures thereof can be cited.

As ethoxylated ethers of fatty acids and glucose or alkylglucose, ethoxylated ethers of fatty acids and methylglucose, and in particular the polyethylene glycol ether of the diester of methylglucose and stearic acid with about 20 moles of ethylene oxide (CTFA name: PEG-20 methyl glucose distearate) such as the product marketed under the name Glucam E-20 distearate by AMERCHOL, the polyethylene glycol ether of the mixture of monoester and diester of methyl-glucose and stearic acid with about 20 moles of ethylene oxide (CTFA name: PEG-20 methyl glucose sesquistearate) and in particular the product marketed under the name Glucamate SSE-20 by AMERCHOL and that marketed under the name Grillocose PSE-20 by GOLDSCHMIDT, and mixtures thereof, can for example be cited.

As sucrose esters, saccharose palmito-stearate, saccharose stearate and saccharose monolaurate can for example be cited.

As sugar ethers, alkylpolyglucosides can be used, and for example decylglucoside such as the product marketed under the name MYDOL 10 by Kao Chemicals, the product marketed under the name PLANTAREN 2000 by Henkel, and the product marketed under the name ORAMIX NS 10 by Seppic, caprylyl/capryl glucoside such as the product marketed under the name ORAMIX CG 110 by Seppic or under the name LUTENSOL GD 70 by BASF, laurylglucoside such as the products marketed under the names PLANTAREN 1200 N and PLANTACARE 1200 by Henkel, coco-glucoside such as the product marketed under the name PLANTACARE 818/UP by Henkel, cetostearyl glucoside possibly mixed with cetostearyl alcohol, marketed for example under the name MONTANOV 68 by Seppic, under the name TEGO-CARE CG90 by Goldschmidt and under the name EMULGADE KE3302 by Henkel, arachidyl glucoside, for example in the form of the mixture of arachidyl and behenyl alcohols and arachidyl glucoside marketed under the name MONTANOV 202 by Seppic, cocoylethylglucoside, for example in the form of the mixture (35/65) with cetyl and stearyl alcohols, marketed under the name MONTANOV 82 by Seppic, and mixtures thereof can in particular be cited.

Mixtures of glycerides of alkoxylated plant oils such as mixtures of ethoxylated (200 EO) palm and copra (7 EO) glycerides can also be cited.

The nonionic surfactant according to the present invention preferably contains alkenyl or a branched $C_{12}$-$C_{22}$ acyl chain such as an oleyl or isostearyl group. More preferably, the nonionic surfactant according to the present invention is PEG-20 glyceryl triisostearate.

According to one of the embodiments of the present invention, the nonionic surfactant may be selected from copolymers of ethylene oxide and of propylene oxide, in particular copolymers of the following formula:

$$HO(C_2H_4O)_a(C_3H_6O)_b(C_2H_4O)_cH$$

in which a, b and c are integers such that a+c ranges from 2 to 100 and b ranges from 14 to 60, and mixtures thereof.

According to one of the embodiments of the present invention, the nonionic surfactant may be selected from silicone surfactants. Non-limiting mention may be made of those disclosed in documents U.S. Pat. Nos. 5,364,633 and 5,411,744.

The silicone surfactant may preferably be a compound of formula (I):

$$R_1-\underset{\underset{CH_3}{|}}{\overset{\overset{CH_3}{|}}{Si}}O-\left[\underset{\underset{CH_3}{|}}{\overset{\overset{CH_3}{|}}{Si}}O\right]_A-\left[\underset{\underset{R_2}{|}}{\overset{\overset{CH_3}{|}}{Si}}O\right]_B-\underset{\underset{CH_3}{|}}{\overset{\overset{CH_3}{|}}{Si}}-R_3 \quad (I)$$

in which:
$R_1$, $R_2$ and $R_3$, independently of each other, represent a $C_1$-$C_6$ alkyl radical or a radical $-(CH_2)_x-(OCH_2CH_2)_y-(OCH_2CH_2CH_2)_y-OR_4$, at least one radical R1, R2 or R3 not being an alkyl radical; R4 being a hydrogen, an alkyl radical or an acyl radical;
A is an integer ranging from 0 to 200;
B is an integer ranging from 0 to 50; with the proviso that A and B are not simultaneously equal to zero;
x is an integer ranging from 1 to 6;
y is an integer ranging from 1 to 30;
z is an integer ranging from 0 to 5.

According to one preferred embodiment of the present invention, in the compound of formula (I), the alkyl radical is a methyl radical, x is an integer ranging from 2 to 6 and y is an integer ranging from 4 to 30.

As examples of silicone surfactants of formula (I), mention may be made of the compounds of formula (II):

$$(CH_3)_3SiO-[(CH_3)_2SiO]_A-(CH_3SiO)_B-Si(CH_3)_3 \\ | \\ (CH_2)_2-(OCH_2CH_2)_y-OH \quad (II)$$

in which A is an integer ranging from 20 to 105, B is an integer ranging from 2 to 10 and y is an integer ranging from 10 to 20.

As examples of silicone surfactants of formula (I), mention may also be made of the compounds of formula (III):

$$H-(OCH_2CH_2)_y-(CH_2)_3-[(CH_3)_2SiO]_{A'}- \\ (CH_2)_3-(CH_2CH_2)_y-OH \quad (III)$$

in which A' and y are integers ranging from 10 to 20.

Compounds of the present invention which may be used are those sold by the company Dow Corning under the names DC 5329, DC 7439-146, DC 2-5695 and Q4-3667. The compounds DC 5329, DC 7439-146 and DC 2-5695 are compounds of formula (II) in which, respectively, A is 22, B is 2 and y is 12; A is 103, B is 10 and y is 12; A is 27, B is 3 and y is 12.

The compound Q4-3667 is a compound of formula (III) in which A is 15 and y is 13.

(Additional Optional Ingredients)

The composition according to the present invention may also include any other optional or additional ingredient(s).

The other optional ingredient(s) may be selected from the group consisting of anionic, cationic, nonionic, or amphoteric polymers; fillers; pigments; inorganic and organic UV filters; peptides and derivatives thereof; protein hydrolyzates; swelling agents and penetrating agents; agents for combating hair loss; anti-dandruff agents; suspending agents; sequestering agents; opacifying agents; dyes; vitamins or provitamins; fragrances; preserving agents, stabilizers; and mixtures thereof.

The composition according to the present invention may include one or several cosmetically acceptable organic solvents, which may be alcohols: in particular monovalent alcohols such as ethyl alcohol, isopropyl alcohol, benzyl alcohol, and phenylethyl alcohol; diols such as ethylene glycol, propylene glycol, and butylene glycol; other polyols such as glycerol, sugar, and βs; and ethers such as ethylene glycol monomethyl, monoethyl, and monobutyl ethers, propylene glycol monomethyl, monoethyl, and monobutyl ethers, and butylene glycol monomethyl, monoethyl, and monobutyl ethers.

The organic solvent(s) may be present in a concentration of from 0.01% to 25% by weight, preferably from 0.1% to 20% by weight, and more preferably from 1% to 15% by weight, relative to the total weight of the composition.

[Form]

It is preferable that the composition according to the present invention be in the form of a liquid at 25° C. and under atmospheric pressure (760 mmHg).

The composition according to the present invention may be in any faun such as a solution, a dispersion, a gel, and a paste.

The composition according to the present invention may be a cosmetic composition. Thus, the cosmetic composition according to the present invention may be intended for application onto a keratin substance. Keratin substance here means a material containing keratin as a main constituent element, and examples thereof include the skin, scalp, nails, lips, hair, and the like. Thus, it is preferable that the cosmetic composition according to the present invention be used for a cosmetic process for the keratin substance, in particular skin.

The composition according to the present invention may preferably be a rinse-off composition. The rinse-off composition can be removed from a keratin substance such as skin, preferably with water.

The composition according to the present invention may preferably be a cleansing composition. The cleansing composition can remove sebum and/or makeup on a keratin substance such as skin from the keratin substance.

The composition according to the present invention may more preferably be a rinse-off cleansing composition. The rinse-off cleansing composition can remove sebum and/or makeup on a keratin substance such as skin, and can be removed from the keratin substance, preferably with water.

The composition according to the present invention can be prepared by mixing the above-described essential and optional ingredients in a conventional manner.

[Process]

The present invention also relates to a cosmetic process for a keratin substrate, such as skin, comprising: applying to the keratin substrate the composition according to the present invention.

It is preferable that the cosmetic process according to the present invention further comprise rinsing off the composition according to the present invention which has been applied onto the keratin substance from the keratin substance.

It is possible that the composition according to the present invention be left on the keratin substance for a certain period of time such as some minutes after being applied onto the keratin substance.

The cosmetic process here means a non-therapeutic cosmetic method, preferably for cleansing the keratin substance such as skin, and more preferably for cleansing sebum and/or makeup on the keratin substance.

[Use]

The present invention also relates to a use of a combination of:
(a) at least one modified starch; and
(b) at least one $C_{13}$-$C_{15}$ fatty acid
in order to increase the deposition on a keratin substance, such as skin, of (c) at least one clay.

In other words, the combination of the ingredients (a) and (b) can enhance the deposition on the keratin substance such as skin of the ingredient (c).

The above explanations for the ingredients (a) to (c) for the composition according to the present invention can also apply to the above ingredients (a) to (c) for the use according to the present invention.

The (a) modified starch and the (b) $C_{13}$-$C_{15}$ fatty acid may form a complex, and preferably the (c) clay is coated with the complex.

The hydrophobicity of the (c) clay can be enhanced by the (a) modified starch and the (b) $C_{13}$-$C_{15}$ fatty acid, preferably a complex formed by the (a) modified starch and the (b) $C_{13}$-$C_{15}$ fatty acid, and more preferably a complex formed by hydrophobic modified starch and myristic acid. Therefore, the (c) clay can deposit more on a keratin substance such as skin, due to hydrophobic-hydrophobic interaction between the (c) clay and the keratin substance. This can result in the increase in the amount of the deposition of the (c) clay on the keratin substance.

Since the use according to the present invention can increase the amount of the deposition of clay on a keratin substance, the use according to the present invention can provide the keratin substance with effects such as long-lasting oil control effects. Also, the increased amount of the deposition of clay on a keratin substance such as skin can provide a smooth feeling to touch for a long period of time.

The above combination can be used in a composition, preferably a cosmetic composition, and more preferably a cleansing cosmetic composition, which may include the optional ingredients such as water, at least one surfactant and at least one additional optional ingredients such as those explained above, in particular at least one acidifying agent and/or at least one basifying agent.

The above composition may be acidic. For example, the pH of the above composition may be less than 7.0, more preferably less than 6.5, and even more preferably less than 6.0. Alternatively, the above composition may be basic. For example, the pH of the above composition may be more than 7.0, more preferably more than 7.5, and even more preferably more than 8.0.

The use according to the present invention may be rephrased as a process for increasing or enhancing the deposition on a keratin substance, such as skin, of (c) at least one clay, comprising applying a combination of the (a) modified starch and the (b) $C_{13}$-$C_{15}$ fatty acid with the (c) clay onto the keratin substance. This process can increase the amount of the deposition of the (c) clay on the keratin substance.

EXAMPLES

The present invention will be described in a more detailed manner by way of examples. However, these examples should not be construed as limiting the scope of the present invention. The examples below are presented as non-limiting illustrations in the field of the present invention.

Example 1 and Comparative Examples 1-3

[Preparations]

Each of the treatment compositions for hair according to Example 1 (Ex. 1) and Comparative Examples 1-3 (Comp. Ex. 1 to Comp. Ex. 3) was prepared by mixing the ingredients shown in Table 1. The numerical values for the amounts of the ingredients are all based on "% by weight" as active raw materials.

TABLE 1

|  | Ex. 1 | Comp. Ex. 1 | Comp. Ex. 2 | Comp. Ex. 3 |
|---|---|---|---|---|
| Potassium Hydroxide | 8.23 | 8.23 | 8.23 | 8.23 |
| Tetrasodium EDTA | 0.05 | 0.05 | 0.05 | 0.05 |
| Kaolin | 20 | 20 | 20 | 20 |
| Zea Mays (Corn) Starch | — | — | — | 1 |
| Corn Starch Modified | 1 | — | 1 | — |
| Phenoxyethanol | 0.5 | 0.5 | 0.5 | 0.5 |
| Butyleneglycol | 3 | 3 | 3 | 3 |
| Water | qsp 100 | qsp 100 | qsp 100 | qsp 100 |
| Glycerin | 10 | 10 | 10 | 10 |
| Caprylyl Glycol | 1 | 1 | 1 | 1 |
| Myristic Acid | 6.33 | 6.33 | — | 6.33 |
| Laurie Acid | 4 | 4 | 4 | 4 |
| Stearic Acid | 3 | 3 | 3 | 3 |
| Glyceryl Stearate | 1 | 1 | 1 | 1 |
| Palmitic Acid | 5 | 5 | 5 | 5 |
| Potassium Cocoyl Glycinate (and) Potassium Cocoate | 10 | 10 | 10 | 10 |
| Stability | Stable | Stable | Unstable | Stable |
| Deposition Feeling | 4.8 | 3.4 | N.A. | 4.0 |
| Long-Lasting Oil Control | 4.8 | 3.2 | N.A. | 3.5 |

*N.A.: Not Available

[Evaluations]
(Stability)

Each of the compositions according to Example 1 and Comparative Examples 1 to 3 was put into an incubator at 45 C±1° C. The aspect of the composition was checked before and after 14 days by visual observation. The results are shown in Table 1. Clear phase separation ("Unstable") was observed for the compositions according to Comparative Example 2. The other compositions showed no phase separation ("Stable").

(Sensory Evaluations)

The compositions according to Example 1 and Comparative Examples 1 to 3 were evaluated with respect to deposition feeling and long-lasting oil control by 5 monitors. Each of the compositions according to Example 1 and Comparative Examples 1 to 3 was applied on the monitors' faces by the monitors themselves and the monitors evaluated deposition feeling and long-lasting oil control by scoring in accordance with the following criteria. The average score is shown in Table 1.

5: Very Good
4: Good
3: Fair
2: Poor
1: Very Poor

It is clear from Table 1 that the composition according to Example 1, which includes a combination of (a) modified starch, (b) $C_{13}$-$C_{15}$ fatty acid, and (c) clay, was stable and was able to provide the best results in terms of deposition feeling and long-lasting oil control.

On the other hand, the composition according to Comparative Example 1, which lacks (a) modified starch but includes (b) $C_{13}$-$C_{15}$ fatty acid and (c) clay, was stable but provided inferior results, as compared to the composition according to Example 1, in terms of deposition feeling and long-lasting oil control.

The composition according to Comparative Example 2, which lacks (b) $C_{13}$-$C_{15}$ fatty acid but includes (a) modified starch and (c) clay, was not stable and could not be evaluated in terms of deposition feeling and long-lasting oil control.

The composition according to Comparative Example 3, which includes unmodified starch, (b) $C_{13}$-$C_{15}$ fatty acid and (c) clay, was stable but provided inferior results, as compared to the composition according to Example 1, in terms of deposition feeling and long-lasting oil control.

The invention claimed is:

1. A composition, comprising:
   (a) at least one modified starch;
   (b) at least one $C_{13}$-$C_{15}$ fatty acid; and
   (c) at least one clay,
   wherein the (a) modified starch and the (b) $C_{13}$-$C_{15}$ fatty acid form a complex.

2. The composition according to claim 1, wherein the (a) modified starch is hydrophobic.

3. The composition according to claim 1, wherein the (a) modified starch is hydroxyalkyl-modified starch.

4. The composition according to claim 1, wherein the (b) $C_{13}$-$C_{15}$ fatty acid is myristic acid.

5. The composition according to claim 1, wherein the (c) clay is kaolin.

6. The composition according to claim 1, wherein the weight ratio of the amount of the (b) $C_{13}$-$C_{15}$ fatty acid/the amount of the (a) modified starch is 1.1 or more.

7. The composition according to claim 1, wherein the (c) clay is coated with the (a) modified starch and the (b) $C_{13}$-$C_{15}$ fatty acid.

8. The composition according to claim 1, wherein
   the amount of the (a) modified starch in the composition is from 0.01% to 15% by weight, relative to the total weight of the composition,
   the amount of the (b) $C_{13}$-$C_{15}$ fatty acid is from 1% to 20% by weight, relative to the total weight of the composition, and
   the amount of the (c) clay is from 1% to 40% by weight, relative to the total weight of the composition.

9. The composition according to claim 1, wherein the composition further comprises (d) water.

10. The composition according to claim 9, wherein the pH of the composition is more than 7.0.

11. The composition according to claim 1, wherein the composition is a cosmetic composition.

12. A cosmetic process for a keratin substance, comprising:
   applying the composition according to claim 1 onto the keratin substance.

13. A method of coating clay, the method comprising:
   combining:
   (a) at least one modified starch; and
   (b) at least one $C_{13}$-$C_{15}$ fatty acid
   with (c) at least one clay in order to increase the deposition on a keratin substance of (c) at least one clay,
   wherein the (a) modified starch and the (b) $C_{13}$-$C_{15}$ fatty acid form a complex.

* * * * *